United States Patent
Pushpangadan et al.

(10) Patent No.: US 7,658,954 B2
(45) Date of Patent: Feb. 9, 2010

(54) SYNERGISTIC ANTIPYRETIC FORMULATION

(75) Inventors: Palpu Pushpangadan, Uttar Pradesh (IN); Ajay Kumar Singh Rawat, Lucknow (IN); Chandana Venkateshwara Rao, Lucknow (IN); Sharad Kumar Srivastava, Lucknow (IN); Sayyada Khatton, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 151 days.

(21) Appl. No.: 11/025,757

(22) Filed: Dec. 29, 2004

(65) Prior Publication Data

US 2006/0141069 A1 Jun. 29, 2006

(51) Int. Cl.
*A61K 36/00* (2006.01)
*A61K 9/00* (2006.01)
*A61K 47/00* (2006.01)

(52) U.S. Cl. ................ 424/725; 424/400; 424/439
(58) Field of Classification Search ........... 424/725, 424/439, 400
See application file for complete search history.

(56) References Cited

U.S. PATENT DOCUMENTS

| 5,683,698 A | * | 11/1997 | Chavali et al. ............ 424/756 |
| 5,856,487 A | * | 1/1999 | Upadhyay et al. ............ 546/48 |
| 2002/0142055 A1 | * | 10/2002 | De Souza et al. ........... 424/762 |
| 2006/0063831 A1 | * | 3/2006 | Hancke Orozco et al. ... 514/473 |

OTHER PUBLICATIONS

Immaculata Iwo et al. (Immunostimulating effect of Pule (Alstonia scholaris) bark extracts, Clinical Hemorheology and Microcirculation, vol. 2000, Issue 23, pp. 177-183).*
Singh (Efficacy of herbal PulmoFlex in bronchial asthma in children, Indian Journal of Indigenous Medicines, vol. 18, No. 2, (1996), pp. 87-93).*

* cited by examiner

*Primary Examiner*—Christopher R Tate
*Assistant Examiner*—Randall Winston
(74) *Attorney, Agent, or Firm*—Foley & Lardner LLP

(57) ABSTRACT

The present invention relates to a synergistic antipyretic formulation comprising extracts of plants *Berberis aristata*, *Tinospora cordifolia*, *Alstonia scholaris*, *Andrographis paniculata* and *Hedychium spicatum*, optionally along with pharmaceutically acceptable additives; its use in treating fever, and lastly, a process for the preparation said synergistic antipyretic formulation.

19 Claims, No Drawings

SYNERGISTIC ANTIPYRETIC FORMULATION

FIELD OF THE INVENTION

The present invention relates to a synergistic antipyretic formulation comprising extracts of plants *Berberis aristata, Tinospora cordifolia, Alstonia scholaris, Andrographis paniculata* and *Hedychium spicatum*, optionally along with pharmaceutically acceptable additives; its use in treating fever, and lastly, a process for the preparation said synergistic antipyretic formulation.

BACKGROUND AND PRIOR ART OF THE INVENTION

Pyrexia during infection produced through the generation of pyrogen (a protein), which increases prostaglandin synthesis in hypothalamus—raising its temperature. Body temperature is normally regulated between 35.8 and 37.2° C. (96.5 and 99° F.) in healthy persons. Omitting disorders that may involve cerebral thermoregulatory centres directly, such as brain tumors, intra cranial hemorrhage or thrombosis, or heat stroke, the disease states may be accompanied by fever. One of the major causes of fever is Malaria. It is a protozoan disease transmitted by the bite of *anopheles* mosquitoes. It is the most important of the parasitic diseases of human being, affecting approximately 200 million people and causing over one million death each year. Dengue fever is an infectious disease carried by mosquitoes and caused by viruses. This fever is also called as break-bone fever as because it causes muscle and joint pain. Accordingly, effect of a wide variety of pharmacological agents have been studied and most validly interpreted as "anti-pyretic". The development of scientifically validated models of yeast-induced fever is vital to the analysis of the functional consequences of pyrexia and to testing the anti-pyretic efficacy of potentially therapeutic drugs. The role of medicinal plants in maintaining the body temperature and acting as anti-pyretic agents is still much underestimated. Besides this, the formulations under investigation have been found to be used as analgesic, muscle relaxant, antioxidant, anti-inflammatory, antiulcer, ophthalmia and antipyretic.

Hitherto, we present a novel synergistic herbal formulation, which contains plants, which have been used for the treatment of pyrexia. Hence a study was undertaken to develop a synergistic combination of plants to develop a novel formulation effective in the treatment of pyrexia.

DETAILS OF THE INGREDIENTS OF THE FORMULATION

*Berberis aristata* Family: Berberidaceae

Botanical Description: *Berberis aristata* DC. is a large deciduous shrub usually 1.8-3.6 m high. Twigs whitish or pale yellowish brown erect cylindrical, smooth and strongly striate. Blaze 5-7.5 mm, bright yellow with coarse reticulate fibres. Leaves 3.8-10×1.5-3.3 cm, obovate or elliptic, entire or spinous-toothed, base gradually narrowed, with prominent reticulate nerves, glossy dark green above and glossy pale green beneath. Flowers numerous, stalked. Inflorescence a simple drooping raceme, bracts small, linear, acuminate. Sepals 8 or 9, imbricate, oval, petaloid, yellow. Petals 6, in two whorls, strongly imbricate, concave, bright yellow veined with two oval linear glands at the base of the lateral veins. Stamens 6 equal, hypogynous, opposite and slightly shorter than the petals. Ovary simple, 1-celled, with a few erect ovules. Style short, Stigma peltate. Fruit a small berry about 7-10 mm, ovoid or oblong ovoid, blue black with a whitish bloom tipped along with the persistent style and stigma.

The roots are thick, woody, yellowish brown, cylindrical, knotty and covered with a thin brittle bark. Bark is internally yellowish brown, rough, closely and rather deeply furrowed. Cut surface bright yellow, rough, fibrous with small fine ridges; root diffused porous, fracture hard; odourless and bitter in taste Medicinal uses: *Berberis aristata* DC., known as 'Daruharidra' in Ayurvedic system of medicine, it is extensively used in various systems of indigenous medicine for treating a variety of ailments such as eye and ear diseases, rheumatism, jaundice, diabetes, stomach disorders, skin disease, malarial fever and as tonic etc. (Watt 1883; Kirtikar and Basu 1933; Anonymous 1948; Nadkarni 1954).

Phytochemistry: The roots and stem bark contains a number of alkaloids, of which the chief active alkaloid is berberine. Besides, berberine, it also contains Oxyberberine, berbamine, aromoline, karachine, palmatine, Oxyacanthine and taxilamine. (Rastogi and Mehrotra, 1993).

Pharmacology: A decoction made from this drug is used as mouthwash for treating swollen gums and toothache (Anonymous 1948). Gilani (1992) reported that the leaves of *B. aristata* could prevent acetaminophen-induced liver damage. Extracts of the fresh root is extensively used as a purgative for children. 50% aqueous alcoholic extract of root is hypoglycemic and anticancerous. Paste of Root-bark is applied for healing ulcers and a combination with opium, rock salt and alum is considered to be a useful anti-inflammatory agent (Ashima Chaterjee 1994). Tripathi (1996) worked out on Hepatopathy in goats, antamoebic effect of a crude drug formulation with *B. aristata* is used against *Entamoeba histolytica* and also to treat allergic disorders. A poly herbal formulation with *B. aristata* and other 5 herbs was evaluated in experimental amoebic liver abscess in golden hamsters and in immunomodulation studies (Sohni et al 1996) Ethno medical investigation carried out by Shah (1971) revealed that the tribal of Kumaun region use the decoction of root for treating eye troubles and boils however Chauhan (1978-79) reported that the decoction is also being for piles, gastric disorders and other allied complaints by Tibetans.

*Tinospora cordifolia* Family: Menispermaceae

Botanical Descriptions: A large glabrous climbing shrub. Stems rather succulent with long filiform, aerial roots arising from branches. Bark; warty, papery thin, creamy white or grey brown. Peels off easily. Wood, soft, perforated. Leaves; membranous, cordate with broad sinus. Pointed at the tip. Flowers; unisexual and greenish, in long clusters. Seeds; curved. Drupes; ovoid, succulent, lustrous, red, pea sized. Fruits; fleshy, one seeded. Flowers during the summer and fruits during the winter. It is found throughout tropical India, ascending to an altitude of 300 m Medicinal Uses: Useful in rheumatism, general debility, seminal weakness, splenic diseases and urinary affections. Fresh plant is considered more efficacious. It is mostly used for preparing a kind of starch known as Guduchi satva or Sat giloe.

Phytochemistry: Sesquiterpene tinocordifolin, sesquiterpene glucoside tinocordifolioside, tinosponone, tinocordioside, cordioside, furanoid diterpenes, a new clerodane furanoditerpene viz. columbin, tinosporaside, an immunologically active arabinogalactan, two phytoecdyyones viz., ecdysterone and makisterone and several glycosides isolated as polyacetates. Other alkaloids viz., jatrorrhizine, palmatine, berberine, tembeterine, phenylpropene disaccharides cordifolioside A, B and C, choline, tinosporic acid, tinosporal, tinosporon, 20-β-hydroxyecdysone, palmatoside C and F, cordifolisides D and E, diterpenoid furanolactones.

Pharmacology: The water and ethanolic extract inhibited the cyclophosphamide induced immunosupression. Aqueous extract of the stem showed anti-inflammatory, analgestic and antipyretic properties in rats. In clinical studies, it also showed immunosuppressive effect in obstructive jaundice patients, antioxidant activity and amelioration of cylcophosphainide-induced toxicity;

*Andrographis paniculata* Family: Acanthaceae

Botanical Descriptions:

It is an erect herb with quadrangular (young) stem, opposite, decussate leaves and white flowers in axillary or terminal panicles or racemes.

Medicinal Uses

Useful in dysentery, dyspepsia, loss of appetite and general debility. It is an ingredient of a number of preparations prescribed in liver diseases. It is a major constituent of *Switraadi lapa*, an effective drug for Vitilago, *Kaalmegha navayas churna* and *Kaalmegha aasava*, especially liver disorders. (Wealth of India, 1965)

*Alstonia scholaris* Family: Apocynaceae

Botanical Descriptions:

The tree grows from 50 to 80 feet high, has a furrowed trunk, oblong stalked leaves up to 6 inches long and 4 inches wide, dispersed in four to six whorls round the stem, their upper side glossy, under side white, nerves running at right angles to the mid-rib. The bark is almost odourless and very bitter, in commerce it is found in irregular fragments ⅛ to ½ inch thick, texture spongy, fracture coarse and short, outside layer rough uneven fissured brownish grey and sometimes blackish spots; inside layer bright buff.

Medicinal Uses

Considered useful in respiratory diseases, chronic diarrhea and advance stages of dysentery. The bark is regarded as a bitter tonic and mild febrifuge, and possesses astringent, anthelmintic and galactogogue properties. It is reported to be employed in heart diseases, asthma, chronic diarrhea, and to stop bleeding of wounds. Bruised and boiled in oil with cottonseed, the bark is applied to the ear for deafness. The fresh bark juice with milk is stated to be administered in leprosy and dyspepsia. In Ayurvedic system, the drug is said to be useful in cancer-like conditions. It is reported to inhibit the multiplication of the potato virus X to the extent of 60-80 percent.

The milky juice or latex is applied to ulcer, sores, tumours and in rheumatic pain, and is used for curing toothache. It is reported to be an antidote for Antiaris-posisoning.

*Hedychium spicatum* Family: Zingiberaceae

Botanical Descriptions:

It is a perennial rhizomatous herb. It grows throughout the plains and in subtropical Himalayan region upto a height of 1000 m in India.

Medicinal Uses

The rhizomes have a strong aromatic odour and bitter taste. They have been used as perfume in tobacco and as insect repellant (Wealth of India, 1965). In local language the rhizomes are commonly known as Kapur Kachari, 'Shati' or 'Ban Haldi'. They have also been reported to be useful for the relief of pain and inflammation (Chopara et al, 1965). In Ayurvedic medicinal texts this herb has been described to be useful, among other things, in the treatment of swelling, asthma, fever and pain. Initial biological screening of the 50% ethanolic extract of the powdered rhizomes revealed its anti-inflammatory and central nervous system depressant activity (Srimal et al 1984).

OBJECTS OF THE PRESENT INVENTION

The main object of the present invention is to develop a synergistic antipyretic formulation comprising extracts of plants *Berberis aristata, Tinospora cordifolia, Alstonia scholaris, Andrographis paniculata* and *Hedychium spicatum*, optionally along with pharmaceutically acceptable additives.

Another main object of the present invention is to develop a method of treating fever in a subject in need thereof using pharmaceutically effective amount of a synergistic antipyretic formulation comprising extracts of plants *Berberis aristata, Tinospora cordifolia, Alstonia scholaris, Andrographis paniculata* and *Hedychium spicatum*

Yet another object of the present invention is to develop a process for the preparation of a synergistic antipyretic formulation comprising extracts of plants *Berberis aristata, Tinospora cordifolia, Alstonia scholaris, Andrographis paniculata* and *Hedychium spicatum*.

SUMMARY OF THE PRESENT INVENTION

The present invention relates to a synergistic antipyretic formulation comprising extracts of plants *Berberis aristata, Tinospora cordifolia, Alstonia scholaris, Andrographis paniculata* and *Hedychium spicatum*, optionally along with pharmaceutically acceptable additives; its use in treating fever, and lastly, a process for the preparation said synergistic antipyretic formulation.

DETAILED DESCRIPTION OF THE PRESENT INVENTION

Accordingly, the present invention relates to a synergistic antipyretic formulation comprising extracts of plants *Berberis aristata, Tinospora cordifolia, Alstonia scholaris, Andrographis paniculata* and *Hedychium spicatum*, optionally along with pharmaceutically acceptable additives; its use in treating fever, and lastly, a process for the preparation said synergistic antipyretic formulation.

In an embodiment of the present invention, wherein the invention relates to a synergistic antipyretic formulation comprising extracts of plants *Berberis aristata, Tinospora cordifolia, Alstonia scholaris, Andrographis paniculata* and *Hedychium spicatum*, optionally along with pharmaceutically acceptable additives.

In yet another embodiment of the present invention, wherein the plant *Berberis aristata* is of concentration ranging between 10-20% wt.

In still another embodiment of the present invention, wherein the concentration of the plant *Berberis aristata* is preferably about 15%.

In still another embodiment of the present invention, wherein the plant *Tinospora cordifolia* is of concentration ranging between 10-20% wt.

In still another embodiment of the present invention, wherein the concentration of the plant *Tinospora cordifolia* is preferably about 15% wt.

In still another embodiment of the present invention, wherein the plant *Alstonia scholaris* is of concentration ranging between 7-13% wt.

In still another embodiment of the present invention, wherein the concentration of the plant *Alstonia scholaris* is preferably about 10% wt.

In still another embodiment of the present invention, wherein the plant *Andrographis paniculata* is of concentration ranging between 7-13% wt.

In still another embodiment of the present invention, wherein the concentration of the plant *Andrographis paniculata* is preferably about 10% wt.

In still another embodiment of the present invention, wherein the plant *Hedychium spicatum* is of concentration ranging between 10-20% wt.

In still another embodiment of the present invention, wherein the concentration of the plant *Hedychium spicatum* is preferably about 15% wt.

In still another embodiment of the present invention, wherein the additives are selected from a group comprising binders and vehicles.

In still another embodiment of the present invention, wherein the present invention relates to a method of treating fever in a subject in need thereof, said method comprising step of administering pharmaceutically effective amount of a synergistic antipyretic formulation comprising extracts of plants *Berberis aristata, Tinospora cordifolia, Alstonia scholaris, Andrographis paniculata* and *Hedychium spicatum*, optionally along with pharmaceutically acceptable additives to the subject.

In still another embodiment of the present invention, wherein the fever is a relapsing fever.

In still another embodiment of the present invention, wherein the fever is dengue fever.

In still another embodiment of the present invention wherein the subject is an animal.

In still another embodiment of the present invention, wherein the subject is a human being.

In still another embodiment of the present invention, wherein the administration is in oral form.

In still another embodiment of the present invention, wherein the invention relates to a process for the preparation of a synergistic antipyretic formulation comprising extracts of plants *Berberis aristata, Tinospora cordifolia, Alstonia scholaris, Andrographis paniculata* and *Hedychium spicatum*, optionally along with pharmaceutically acceptable additives to the subject, said process comprising steps of:
powdering dried parts of the plants,
extracting the powder with an organic solvent,
concentrating the extract under reduced pressure and
lyophilizing the concentrated extract to obtain the formulation.

In still another embodiment of the present invention, wherein the plant parts are selected from a group comprising leaf, root and stem.

In still another embodiment of the present invention, wherein the organic solvent is alcohol.

In still another embodiment of the present invention, wherein the organic solvent is ethanol.

In still another embodiment of the present invention, wherein the extraction is at temperature ranging between 25-35° C.

In still another embodiment of the present invention, wherein the concentrating the extract at temperature ranging between 40-60° C.

In still another embodiment of the present invention, wherein the lyophilizing leads to complete removal of solvent.

Accordingly, the present invention provides a novel antipyretic dosage form for the treatment of pyrexia such as relapsing fever and dengue herbal synergistic formulation(s) comprising:

In an embodiment of the present invention, a herbal antipyretic health protective herbal formulation used in treatment of relapsing fever and dengue condition(s) of synergistic formulation(s) containing extracts of plants in pharmacologically effective form.

In yet another embodiment of the present invention, said composition is synergistic mixture of plants extract having high antioxidant, cooling, analgesic and anti inflammatory properties.

In yet another embodiment of the present invention, the use according to claim 1 wherein said composition as a syrup of oral dosage form.

In yet another embodiment of the present invention, the use according to claim 1 wherein said formulation having the property of decreasing the body temperature and used in treatment of relapsing fever or dengue.

In yet another embodiment of the present invention, wherein the extract(s) of *Berberis aristata, Tinospora cordifolia, Alstonia scholaris, Andrographis paniculata* and *Hedychium spicatum*.

In yet another embodiment of the present invention, herbal formulations is used to cure jaundice, skin diseases, ophthalmia, diuretic, stomachic and aphrodisacs.

In yet another embodiment of the present invention, herbal formulation (s) wherein the said composition is synergistic mixture of plant extracts having high antioxidant, anti inflammatory and analgesic properties.

In yet another embodiment of the present invention, herbal formulations the formulation is used to cure gonorrhea, rash, myalgia and arthralgia.

In yet another embodiment of the present invention, herbal formulations the formulation used to cure nausea, vomiting and enlarged lymph nodes.

In yet another embodiment of the present invention, herbal formulations the formulation is used to cure gastric disorder as ulcer, diarrhea and gastric pain.

In yet another embodiment of the present invention, herbal formulation(s) the formulation further comprises glucoside, alkaloidal constituents.

In yet another embodiment of the present invention, herbal formulation(s) wherein the formulation further comprises berberine and alkaloid.

In yet another embodiment of the present invention, herbal formulation(s) the formulation further comprises three cristaline substances, two bitter principles and a neutral fatty alcohol.

In yet another embodiment of the present invention, herbal formulation(s) wherein the formulation further comprises a bitter glucoside giloin (mp 226-28° C.).

In yet another embodiment of the present invention, herbal formulation(s) wherein the formulation further comprises non glucosidal bitter substance giloinin (mp. 210-12° C.).

In yet another embodiment of the present invention, herbal formulation(s) further comprises gilo-sterol (mp 192-93° C.).

In yet another embodiment of the present invention, wherein the formulation further comprises tinosporon, tinosporic acid and tinosporol.

In yet another embodiment of the present invention, herbal formulation(s) yield a starch, which is used a tonic in several diseases causing debility.

In yet another embodiment of the present invention, herbal formulation(s) is rich in protein.

In yet another embodiment of the present invention, herbal formulation(s) is rich in calcium and phosphorus.

In yet another embodiment of the present invention, herbal formulation(s) wherein the extracts of the plants are mixed in the ratio *Berberis aristata, Tinospora cordifolia, Alstonia scholaris, Andrographis paniculata* and *Hedychium spicatum* along with conventional additives to form an oral dosage form.

In yet another embodiment of the present invention, herbal formulation(s) as claimed in claim 1 wherein said composition in an oral dosage form selected from a group consisting of a syrup, tablet, capsule and a powder.

In yet another embodiment of the present invention, herbal formulation(s) wherein the extracts of plants are 50% aqueous alcoholic extract.

In yet another embodiment of the present invention, herbal formulation(s) wherein the alcohol used is ethanol.

In yet another embodiment of the present invention, herbal formulation(s) comprises about 25-50% wt of the total formulation.

In yet another embodiment of the present invention, herbal formulation(s) wherein the plant extracts are obtained: from plant parts selected from stems.

In yet another embodiment of the present invention, herbal formulation(s) wherein the binders used are starch, starch paste, gum acacia and car boxy methyl cellulose.

In yet another embodiment of the present invention, wherein the 66.7% w/w sugar syrup is used as a vehicle.

In yet another embodiment of the present invention, wherein the formulation is used in treating pyrexia, and also in dengue.

In yet another embodiment of the present invention, a method of preparing a herbal formulation as claimed in claim 1 wherein the said method comprising:

Obtaining the part of medicinal plants from a group comprising leaves, root and aerial parts.

Drying the plant material in shade.

Powdering the dried plant material to a coarse powder.

Extracting the powdered dried plant material with (40-50% aqueous ethanol) at 25-35° C.

Extracting the plant material with the aqueous alcohol in the ratio of 1:8 to 1:15 for 4-7 days Concentrating the obtained extract at under reduced pressure at 40-60° C.

Lyophilising the concentrated extract for complete removal of solvent.

In yet another embodiment of the present invention, herbal formulation(s) the formulation immediately relieves stomach pain and body temperature by controlling intrleukin-1.

In yet another embodiment of the present invention, herbal formulation(s) wherein the formulation at a dose of 50 mg/kg in yeast induced pyrexia shows significant effect in reducing the raised temperature.

In yet another embodiment of the present invention, herbal formulation(s) the formulation in yeast induced pyrexia shows the maximum antipyretic as well as analgesic activity.

In yet another embodiment of the present invention, herbal formulation(s) the formulation in yeast induced pyrexia shows the anti inflammatory effect.

In yet another embodiment of the present invention, herbal formulation(s) the formulation at a higher doses showed there are no significant changes in the hematological changes.

In yet another embodiment of the present invention, herbal formulation(s) the formulation at a higher doses showed there is no changes in sub acute toxicity studies and gross behavioral changes.

In yet another embodiment of the present invention, herbal formulation(s) the formulation at a higher doses showed there are no changes in organ weights in the yeast induced pyrexia of formulation.

| FORMULATION (F1) | |
| --- | --- |
| *Tinospora cordifolia* | 10% |
| Preservative/Sodium banzoate | 0.001% |
| Simple syrup | Qs to make volume 100% |
| FORMULATION (F2) | |
| *Berberis aristata*. | 10% |
| Preservative/Sodium banzoate | 0.001% |
| Simple syrup | Qs to make volume 100% |
| FORMULATION (F3) | |
| *Berberis aristata* | 15% |
| *Tinospora cordifolia* | 15% |
| Preservative/Sodium banzoate | 0.001% |
| Simple syrup | Qs to make volume 100% |
| FORMULATION (F4) | |
| *Berberis aristata* | 15% |
| *Tinospora cordifolia* | 15% |
| *Alstonia scholaris* | 10% |
| Preservative/Sodium banzoate | 0.001% |
| Simple syrup | Qs to make volume 100% |
| FORMULATION (F5) | |
| *Berberis aristata* | 15% |
| *Tinospora cordifolia* | 15% |
| *Alstonia scholaris* | 10% |
| *Andrographis paniculata* | 10% |
| Preservative/Sodium banzoate | 0.001% |
| Simple syrup | Qs to make volume 100% |
| FORMULATION (F6) | |
| *Berberis aristata* | 15% |
| *Tinospora cordifolia* | 15% |
| *Alstonia scholaris* | 10% |
| *Andrographis paniculata* | 10% |
| *Hedychium spicatum* | 15% |
| Preservative/Sodium banzoate | 0.001% |
| Simple syrup | Qs to make volume 100% |

TABLE 1

Effect of the formulation(s) on normal body temperature

| Treatment | Rectal temperature (° C.) before and after treatment | | | | | |
|---|---|---|---|---|---|---|
| (mg/kg) | 0 h | 1 h | 2 h | 3 h | 4 h | 5 h |
| Control (10 ml/kg) CMC | 37.4 ± 0.1 | 37.3 ± 0.2 | 37.4 ± 0.1 | 37.3 ± 0.1 | 37.4 ± 0.1 | 37.2 ± 0.1 |
| Formulation (F1) | 37.5 ± 0.1 | 37.4 ± 0.2 | 37.5 ± 0.1 | 36.5 ± 0.1 | 36.8 ± 0.2 | 36.9 ± 0.2 |
| Formulation (F2) | 37.2 ± 0.2 | 37.3 ± 0.3 | 37.3 ± 0.1 | 37.2 ± 0.1 | 37.0 ± 0.1 | 36.5 ± 0.2 |
| Formulation (F3) | 37.4 ± 0.2 | 37.4 ± 0.4 | 37.4 ± 0.1 | 37.3 ± 0.1 | 37.1 ± 0.2 | 37.1 ± 0.1 |
| Formulation (F4) | 37.3 ± 0.2 | 37.2 ± 0.3 | 37.1 ± 0.1 | 37.1 ± 0.1 | 36.9 ± 0.2 | 36.9 ± 0.2 |
| Formulation (F5) | 37.2 ± 0.2 | 37.3 ± 0.3 | 37.0 ± 0.2 | 37.2 ± 0.1 | 37.0 ± 0.2 | 37.0 ± 0.2 |
| Formulation (F6) | 37.5 ± 0.3 | 37.2 ± 0.2 | 37.1 ± 0.2 | 37.1 ± 0.2 | 37.3 ± 0.2 | 37.2 ± 0.2 |

Values are mean ± SEM for six rats.
F1 formulation contains *Tinospora cordifolia*
F2 formulation contains *Berberis aristata*
F3 formulation contains *Tinospora cordifolia* (15%) plus *Berberis aristata* (15%)
F4 formulation contains *Tinospora cordifolia* (15%) plus *Berberis aristata* (15%) plus *Alstonia scholaris*.
F5 formulation contains *Tinospora cordifolia* (15%) plus *Berberis aristata* (15%) plus *Alstonia scholaris* (10%) and *Andrographis paniculata* (10%).
F6 formulation contains *Tinospora cordifolia* (15%) plus *Berberis aristata* (15%) plus *Alstonia scholaris* (10%), *Andrographis paniculata* (10%) and *Hedychium spicatum* (15%).

The table 1 represents the effect of formulation F1, F2, F3 and F4 on normal body temperature in rats and results states that there is no effective chance or no change in normal body temperature after treating with the formulation(s).

TABLE 2

Effect of fever reducing in dengue and as antipyretic formulation on yeast induced pyrexia in rats

| Treatment | Rectal temperature (° C.) before and after treatment | | | | |
|---|---|---|---|---|---|
| (mg/kg) | 0 h | 1 h | 2 h | 3 h | 4 h |
| Control (10 ml/kg) CMC | 37.7 ± 0.2 | 38.9 ± 0.1 | 39.3 ± 0.1 | 39.2 ± 0.1 | 39.1 ± 0.2 |
| Formulation F1 | 37.7 ± 0.2 | 38.7 ± 0.2 | 38.2 ± 0.2 | 38.9 ± 0.2 | 39.3 ± 0.2 |
| Formulation F2 | 37.8 ± 0.2 | 38.8 ± 0.2 | 38.9 ± 0.2 | 38.9 ± 0.2 | 37.8 ± 0.2 |
| Formulation F3 | 37.8 ± 0.3 | 39.1 ± 0.3 | 39.2 ± 0.3 | 37.9 ± 0.3 | 37.7 ± 0.2 |
| Formulation F4 | 37.6 ± 0.2 | 39.0 ± 0.2 | 38.0 ± 0.3 | 37.8 ± 0.2$^b$ | 37.7 ± 0.2 |
| Formulation F5 | 37.5 ± 0.2 | 38.1 ± 0.1 | 37.8 ± 0.2$^b$ | 37.6 ± 0.2$^b$ | 37.5 ± 0.2$^b$ |
| Formulation F6 | 37.6 ± 0.2 | 37.8 ± 0.2$^b$ | 37.3 ± 0.2$^b$ | 37.0 ± 0.2$^b$ | 37.0 ± 0.2$^b$ |
| Paracetamol 150 | 37.7 ± 0.2 | 39.0 ± 0.2 | 38.1 ± 0.3 | 37.7 ± 0.2$^b$ | 37.6 ± 0.2 |

Values are mean ± SEM for six rats.
P: $^a$<0.01 and $^b$<0.001 compared to basal value of respective group.
F1 formulation contains *Tinospora cordifolia*
F2 formulation contains *Berberis aristata*
F3 formulation contains *Tinospora cordifolia* (15%) plus *Berberis aristata* (15%)
F4 formulation contains *Tinospora cordifolia* (15%) plus *Berberis aristata* (15%) plus *Alstonia scholaris*.
F5 formulation contains *Tinospora cordifolia* (15%) plus *Berberis aristata* (15%) plus *Alstonia scholaris* (10%) and *Andrographis paniculata* (10%).
F6 formulation contains *Tinospora cordifolia* (15%) plus *Berberis aristata* (15%) plus *Alstonia scholaris* (10%), *Andrographis paniculata* (10%) and *Hedychium spicatum* (15%).

The results of the table 2 represents a significant decrease in the raised temperature with the formulation 5 and 6 containing all the components. Formulation F5 at 2 h, while F6 at 1 h itself reduced the raised temperature or controlled to bring down to normal body temperature. But the significance is high with the F6 (P<0.01). Therefore F6 is highly effective than other formulations containg all the components.

Important table 2 shows that the study was performed in fever suffering rats. For example 38.9±0.1 at 1 hour (Control) treated with formulation F6 significantly reduced to 37.8±0.2. Where as the formulation F1 to F5 did not significantly reduced the fever at one hour. Therefore F6 is having promising activity which is novel.

F1 formulation contains *Tinospora cordifolia*

F2 formulation contains *Berberis aristata*

F3 formulation contains *Tinospora cordifolia* (15%) plus *Berberis aristata* (15%)

F4 formulation contains Tinospora cordifolia (15%) plus Berberis aristata (15%) plus *Alstonia scholaris*.

F5 formulation contains *Tinospora cordifolia* (15%) plus *Berberis aristata* (15%) plus *Alstonia scholaris* (10%) and *Andrographis paniculata* (10%).

F6 formulation contains *Tinospora cordifolia* (15%) plus *Berberis aristata* (15%) plus *Alstonia scholaris* (10%), *Andrographis paniculata* (10%) and *Hedychium spicatum* (15%).

Results of Table 1 States

The table 1 represents the effect of formulation F1, F2, F3 and F4 on normal body temperature in rats and results states that there is no effective chance or no change in normal body temperature after treating with the formulation(s).

Results of Table 2 States

The results of the table 2 represents a significant decrease in the raised temperature with the formulation 5 and 6 containing all the components. Formulation F5 at 2 h, while F6 at 1 h itself reduced the raised temperature or controlled to bring down to normal body temperature. But the significance is high with the F6 ($P<0.01$). Therefore F6 is highly effective than other formulations contains all the components.

TABLE 3

Organ weight of rats in sub acute toxicity of fever reducing formulation

| Treatment (mg/kg) | Lung | Heart | Liver | Spleen | Adrenal | Kidney | Ovary |
|---|---|---|---|---|---|---|---|
| Control | 0.51 ± 0.02 | 0.42 ± 0.01 | 3.17 ± 0.16 | 0.28 ± 0.01 | 0.02 ± 0.00 | 0.43 ± 0.03 | 0.03 ± 0.00 |
| Formulation F4 1 g | 0.50 ± 0.02 | 0.40 ± 0.01 | 3.28 ± 0.15 | 0.29 ± 0.01 | 0.02 ± 0.00 | 0.45 ± 0.02 | 0.04 ± 0.00 |
| Formulation F5 1 g | 0.48 ± 0.02 | 0.41 ± 0.01 | 3.31 ± 0.19 | 0.29 ± 0.01 | 0.02 ± 0.00 | 0.45 ± 0.02 | 0.04 ± 0.00 |
| Formulation F6 1 g | 0.49 ± 0.02 | 0.40 ± 0.01 | 3.29 ± 0.20 | 0.31 ± 0.01 | 0.02 ± 0.00 | 0.46 ± 0.02 | 0.04 ± 0.00 |

F4 formulation contains *Tinospora cordifolia* (15%) plus *Berberis aristata* (15%)
F5 formulation contains *Tinospora cordifolia* (15%) plus *Berberis aristata* (15%) plus *Alstonia scholaris* (10%) and *Andrographis paniculata* (10%).
F6 formulation contains *Tinospora cordifolia* (15%) plus *Berberis aristata* (15%) plus *Alstonia scholaris* (10%), *Andrographis paniculata* (10%) and *Hedychium spicatum* (15%).

CMC—Carboxy methyl cellulose is the solvent given in control 10 ml/kg orally.

REFERENCES CITED

1. U.S. Pat. No. 6,610,713 Aug. 26, 2003 Tracey
2. U.S. Pat. No. 6,573,259 Jun. 3, 2003 Golec, et al
3. Smith et al. J. Ethnopharmacology and experimental therapeutics. 54, pp346, 1935.
4. Anshu Rathi et al. Natural product sciences, 9(3), 195-199, 2003.
5. Rao et al. Acta Pharmaceutica Turcica, 45, 85-91, 2003.
6. Remington, The science and practice of pharmacy, 19th edition, Vol. II. pp. 1635, 1995.
7. Anonymous, The Wealth of India, I, 114-119, PID, CSIR; New Delhi; 1965.
8. Bently, R., and Trimen, H., Medicinal Plants I, 16, International Book Distributors, Dehradun; 1983.
9. Chatterjee, Ashima, Parkrashi, S. C. The Treatise of Indian Medicinal Plants I, PID, CSIR, New Delhi; 1994.
10. Chauhan, N. S., Uniyal, M. R. and Sannad, B. N., A preliminary study of the Indigenous drugs used at the Tibetan Medicinal Centre, Dharmshala (H. P.); *Nagarjun* 22, 190-193; 1978-79.
11. Chopra, R. N., Chopra, T. C., Hand K. L. and Kapoor, L. D., Chopra's Indigenous Drugs of India, 284. U. N. Phar and sons Pvt. Ltd.; 1958.
12. Gilani, A. H., Janbar, K. H., Prevention of acetaminophen-Induced liver damage by *Berberis aristata* leaves. *Biochem Soc. Trans* 20(4); 347 s; 1992.
13. Kirtikar, K. R. and Basu, B. D., Indian Medicinal Plants I, Lalit Mohan Basu and Co., Allahabad; 1933.
14. Rastogi, R. P. and Mehrotra, B. N., Compendium of Indian Medicinal Plants, Vol. 3 CDRI, Lucknow and PID CSIR, New Delhi; 1993.
15. Srimal, R C, Sharma S C and Tandon J S, Anti-inflamatory and other pharmacological effects of *Hedychium spicatum* (Buch-Hem). *Ind. J. Pharmac.* 143-147; 1984.
16. Shah, N. C., Joshi, M. C., An Ethnobotanical study of the Kumaon Region of India; *Eco. Botany* 25, 414-422; 1971.
17. Sohni, Y. R., Bhatt, R. M., Activity of a crude extract formulation in experimental hepatic amoebiasis and in immunomodulation studies, *J Ethnopharmacol* 54 (2-3) 119-124; 1996.
18. Tripathi, Y. B. and Shukla, S. D., *Berberis aristata* inhibits PAF induced aggregation of rabbit platelets; *Phytotherapy Research* 10(7); 628-630; 1996.
19. Watt, G., Economic products of India V, The superintendent of Government Printing, India; 1883.

The invention claimed is:

1. An antipyretic formulation comprising extracts of plants *Berberis aristata* (10-20 wt %), *Tinospora cordifolia* (10-20 wt %), *Alstonia scholaris* (7-13 wt %), *Andrographis paniculata* (7-13 wt %) and *Hedychium spicatum* (10-20 wt %), optionally along with pharmaceutically acceptable additives, wherein the formulation is capable of reducing fever.

2. The formulation as claimed in claim 1, wherein the concentration of the plant *Berberis aristata* is preferably about 15% wt.

3. The formulation as claimed in claim 1, wherein the concentration of the plant *Tinospora cordifolia* is preferably about 15% wt.

4. The formulation as claimed in claim 1, wherein the concentration of the plant *Alstonia scholaris* is preferably about 10% wt.

5. The formulation as claimed in claim 1, wherein the concentration of the plant *Andrographis paniculata* is preferably about 10% wt.

6. The formulation as claimed in claim 1, wherein the concentration of the plant *Hedychium spicatum* is preferably about 15% wt.

7. A method of treating fever in a subject in need thereof, said method comprising the step of administering pharmaceutically effective amount of an antipyretic formulation comprising extracts of plants *Berberis aristata* (10-20 wt %), *Tinospora cordifolia* (10-20 wt %), *Alstonia scholaris* (7-13 wt %), *Andrographis paniculata* (7-13 wt %) and *Hedychium spicatum* (10-20 wt %), optionally along with pharmaceutically acceptable additives to the subject.

8. The method as claimed in claim 7, wherein the fever is a relapsing fever.

9. The method as claimed in claim 7, wherein the fever is dengue fever.

10. The method as claimed in claim 7, wherein the subject is an animal.

11. The method as claimed in claim 7, wherein the subject is a human.

12. The method as claimed in claim 7, wherein the administration is in oral form.

13. A process for the preparation of the antipyretic formulation of claim 1 comprising the steps of:

a. powdering dried parts of the plants,
   b. extracting suitable amounts of the plant powders with an organic solvent,
   c. concentrating the extracts under reduced pressure,
   d. lyophilizing the concentrated extracts to obtain the formulation, and
   e. optionally adding one or more pharmaceutically acceptable additives thereto.

14. The process as claimed in claim 13, wherein the plant parts are selected from a group comprising leaf, roof and stem.

15. The process as claimed in claim 13, wherein the organic solvent is alcohol.

16. The process as claimed in claim 13, wherein the organic solvent is ethanol.

17. The process as claimed in claim 13, wherein the extraction is at temperature ranging between 25-35 degree celcius.

18. The process as claimed in claim 13, wherein the concentrating the extract at temperature ranging between 40-60 degree celcius.

19. The process as claimed in claim 13, wherein the lyophilizing leads to complete removal of the solvent.

* * * * *

UNITED STATES PATENT AND TRADEMARK OFFICE
CERTIFICATE OF CORRECTION

PATENT NO. : 7,658,954 B2
APPLICATION NO. : 11/025757
DATED : February 9, 2010
INVENTOR(S) : Palpu Pushpangadan et al.

It is certified that error appears in the above-identified patent and that said Letters Patent is hereby corrected as shown below:

ON THE TITLE PAGE, Item (75) should read:

(75) Inventors: Palpu PUSHPANGADAN, Uttar Pradesh (IN);
Ajay Kumar Singh RAWAR, Lucknow (IN);
Chandana Venkateshwara RAO, Lucknow (IN);
Sharad Kumar SRIVASTAVA, Lucknow (IN);
Sayyada KHATOON, Lucknow (IN);

Signed and Sealed this

Second Day of November, 2010

David J. Kappos
*Director of the United States Patent and Trademark Office*